US00PP20715P3

(12) United States Plant Patent
Ui

(10) Patent No.: US PP20,715 P3
(45) Date of Patent: Feb. 2, 2010

(54) ***OSTEOSPERMUM* PLANT NAMED 'SAKOST190'**

(50) Latin Name: *Osteospermum hybrida*
Varietal Denomination: SAKOST190

(75) Inventor: Akinobu Ui, Iwata (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/157,665

(22) Filed: Jun. 12, 2008

(65) Prior Publication Data

US 2009/0313735 P1 Dec. 17, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette Para
*Assistant Examiner*—Louanne C Krawczewicz Myers
(74) *Attorney, Agent, or Firm*—Jondle & Associates, P.C.

(57) ABSTRACT

A new *Osteospermum* plant particularly distinguished by having yellow-white flowers with violet-blue to purple centers, compact growth habit and a very vigorous performance under high temperature and humidity levels, is disclosed.

1 Drawing Sheet

Genus and species: *Osteospermum hybrida.*
Variety denomination: 'SAKOST190'.

BACKGROUND OF THE NEW PLANT

'SAKOST190' originated from a hybridization of the female parent, the proprietary hybrid *Osteospermum* breeding line 'V-59', having pink-white bicolour flowers (unpatented) and the male parent, the proprietary hybrid *Osteospermum* line 'SL-4', having a lemon-yellow flower color (unpatented) in a cultivated area (greenhouse) in Kakegawa, Japan.

In 2001, the two *Osteospermum* lines were crossed and 37 ovules were removed from flowers on the female parent and cultured by standard ovule culture techniques. A total of 10 plantlets were developed. The 10 $F_1$ hybrid plantlets were transplanted to soilless media for greenhouse culture and acclimatization. In 2002, the breeder evaluated the plants in pots and the plants were creamy pink in flower color and demonstrated vigorous plant growth and earliness to flower. Out of the 10 $F_1$ lines, the breeder selected line 'K5-350' which has a cream to shell pink flower color with a plant structure with minimal branching, vigorous performance, earliness to flower and maintains its ability to flower under high temperature conditions.

In fall 2003, the line 'K5-350' was vegetatively propagated with cuttings and reevaluated in an open field and a greenhouse. The breeder confirmed the stability of the distinct characteristics of this variety. The selection subsequently was named 'SAKOST190' and found to reproduce true to type in successive generations of asexual propagation by vegetative cuttings in an open field and a greenhouse in Salinas, Calif.

SUMMARY OF THE INVENTION

The following are the most outstanding and distinguishing characteristics of this new cultivar when grown under normal horticultural practices in Salinas, Calif.

1. Yellow-white flowers with violet-blue to purple centers;
2. Compact growth habit; and 3. Very vigorous performance under high temperature and humidity levels.

DESCRIPTION OF THE PHOTOGRAPHS

This new *Osteospermum* plant is illustrated by the accompanying photographs which show the plant's overall plant habit including form, foliage and flowers. The photographs are of a plant grown 3 months from transplant date and four and a half months from stick date in six inch pots from rooted cuttings in Salinas, Calif. in the spring of 2008. The colors shown are as true as can be reasonably obtained by conventional photographic procedures.

Figure 1:
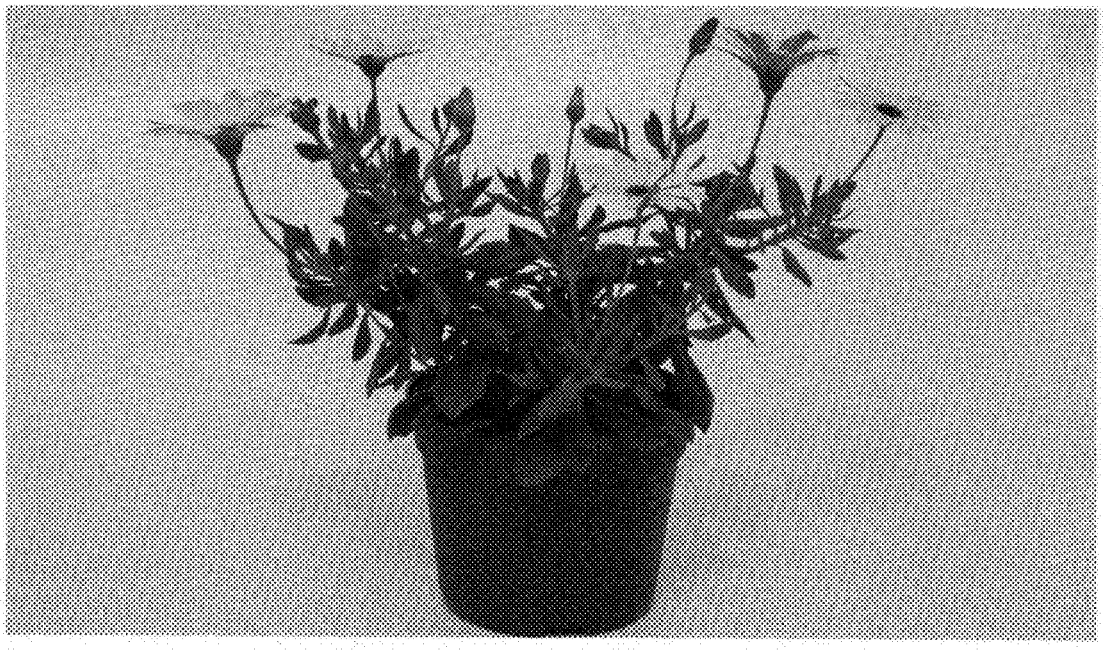
Figure 2:
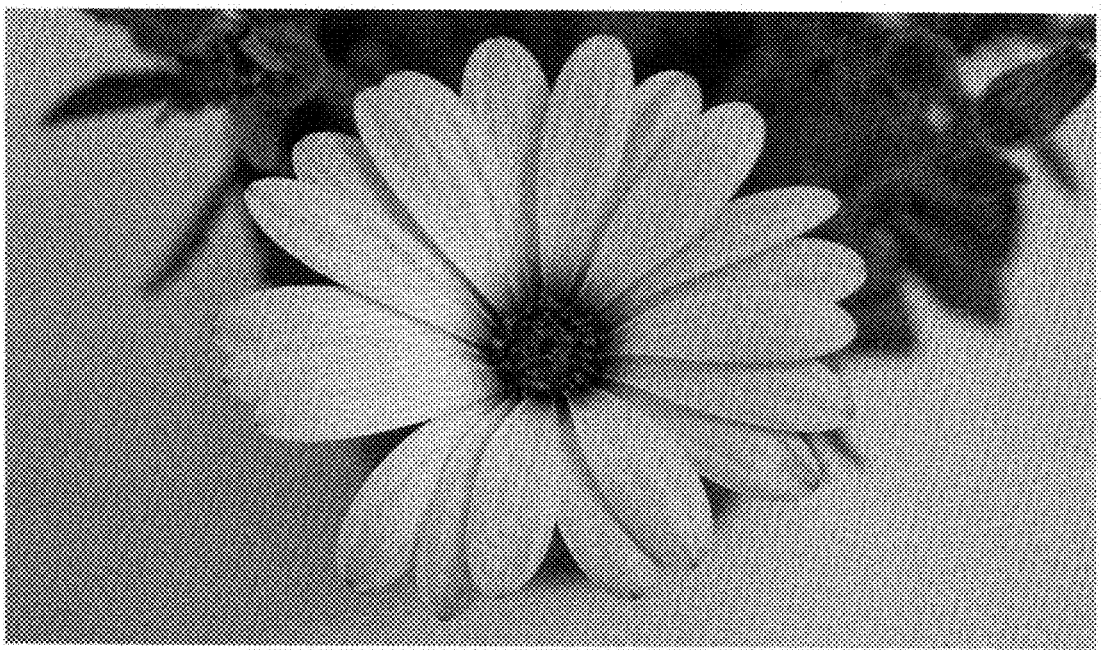

FIG. 1 shows overall plant habit of the plant grown in a pot.
FIG. 2 shows the mature inflorescence of the plant.

DESCRIPTION OF THE NEW CULTIVAR

The following detailed descriptions set forth the distinctive characteristics of 'SAKOST190'. The data which define these characteristics were collected from asexual reproductions carried out in Salinas, Calif. Data was collected on plants grown approximately three months from transplant date and four and a half months from stick date into 6-inch pots under greenhouse conditions in Salinas, Calif. Color references are to The R.H.S. Colour Chart of The Royal Horticultural Society of London (R.H.S.), $4^{th}$ edition.

DESCRIPTION OF THE NEW PLANT

Classification:

*Family.*—Compositae.
*Botanical.*—*Osteospermum hybrida.*
*Denomination.*—'SAKOST190'.

Parentage:

*Female parent.*—A hybrid proprietary *Osteospermum* line 'V-59', having a pink-white bicolor flower (unpatented).

*Male parent.*—A hybrid proprietary *Osteospermum* line 'SL-4', having a lemon-yellow flower color (unpatented).

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW root-inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150–200 ppm fertilizer solution using 18-8-18 fertilizer. The soil is allowed to dry between watering. During the first few weeks after transplanting, the plants should have evening temperatures around 15°–18° C. for good root growth. When plants reach 7.5 cm to 10.0 cm in height they are pinched back to 5–6 leaves to promote branching. Spring and summer daytime high temperatures in Salinas, Calif., where the data was collected, range from 16° C. to 25° C.

*Time to bloom from propagation.*—Approximately four weeks when rooted vegetative cuttings are transferred to a 16 cm diameter pot. Flowering season is all year in the United States. Vernalization is not required to induce flowering.

Plant description:

*Habit.*—Compact.
*Life cycle.*—Perennial.
*Form.*—Less branching.
*Height* (*from soil line to top of foliage*).—23 cm.
*Width.*—40 cm to 45 cm.
*Roots.*—Dense and fibrous.

Stems:

*General.*—Stem is circular in cross section.
*Internode length.*—1.0 cm to 2.0 cm.
*Stem shape.*—Round.
*Stem diameter.*—0.4 cm.
*Stem color.*—RHS 138B (Green).
*Stem length.*—8.0 cm.
*Pubescence.*—Moderate.
*Pubescence shape.*—Linear, short and fuzzy in appearance.
*Pubescence color.*—RHS N155A (White).
*Anthocyanin color.*—RHS N77C (Purple).

Leaves:

*Arrangement.*—Alternate.
*Shape.*—Oblanceolate.
*Apex.*—Acute.
*Base.*—Attenuate.
*Margin.*—Serrate.
*Venation.*—Anastomosing.
*Surface* (*both surfaces*).—Dull.
*Surface pubescence* (*both surfaces*).—Slight pubescence.
*Length.*—6.0 cm.
*Width.*—3.0 cm.
*Thickness.*—Less than 0.1 cm.
*Internode length.*—1.0 cm.
*Color.*—Upper surface: RHS 138A (Green). Lower surface: RHS 138B (Green).
*Venation color* (*both surfaces*).—RHS 139D (Green).
*Petiole.*—Length: 6.0 cm. Diameter: 2.0 cm. Color: RHS 143C (Yellow-green). Texture and appearance: Slightly pubescent, dull.

Inflorescence:

*Type.*—Capitulum (head); disc florets are perfect and ray florets are carpellate.
*Flowering habit.*—Determinate.
*Flowering season.*—Approximately from February to September.
*Quantity of inflorescences per plant.*—About 100 to 200 inflorescences per plant at full maturity.
*Lastingness of flowers.*—3 to 4 days.
*Fragrance.*—None.
*Seed production.*—None observed.
*Receptacle depth.*—1.0 cm.
*Receptacle diameter.*—10.0 cm.
*Diameter.*—8.0 cm.
*Depth.*—2.0 cm to 2.5 cm.
*Ray floret number.*—19 per inflorescence.
*Disc diameter.*—1.5 cm.
*Disc floret number.*—10 to 20 per inflorescence.
*Peduncle length.*—6.0 cm from inflorescence to first node.
*Peduncle diameter.*—0.2 cm.
*Peduncle color.*—RHS 143C (Green).
*Peduncle texture.*—Dull, slight pubescence.
*Phyllaries.*—Arrangement: 19 per inflorescence, free, arranged symmetrically. Length: 1.0 cm to 1.5 cm. Width: 0.1 cm to 0.2 cm. Apex: Acute. Base: Attenuate. Margin: Entire. Shape: Linear, acute. Color (Both surfaces): RHS 138A (Green) with RHS 143C (Green) at the edge. Surface texture (Both surfaces): Smooth (not pubescent).
*Bud.*—Diameter: 1.0 cm. Length: 1.0 cm. Shape: Round with pointed tips. Surface texture: Smooth. Color: RHS N92B (Violet-blue). Hardiness: Tough, tolerant to high temperatures and humidity.

Ray florets (ligules):

*Corolla.*—Only the outer row of florets are the ray florets.
*Number of ray florets per inflorescence.*—19.
*Length.*—4.0 cm to 4.5 cm.
*Width.*—1.0 cm to 1.2 cm.
*Shape.*—Lanceolate.
*Apex.*—Obtuse.
*Base.*—Attenuate.
*Margin.*—Entire.
*Color.*—Upper surface: RHS 158C (Yellow-white) with RHS N78C (Purple) at base and RHS N92D (Violet-blue) at the bottom of the base; streaks of RHS N78D (Purple) on the ray floret and the tip of the ray floret. Lower surface: RHS 164C (Greyed-orange) with streaks of RHS N187B (Greyed-purple) and RHS 93C (Violet-blue) at base.
*Pubescence.*—Glabrous.
*Ovary.*—Superior.
*Ovary color.*—RHS 92A (Violet-blue).
*Pistil form.*—One style with two stigma branches.
*Pistil length.*—0.2 cm.
*Stigma color.*—RHS N92A (Violet-purple).
*Stigma shape.*—Circular (in cross-section).
*Stigma length.*—0.1 cm.
*Style color.*—RHS N78C (Purple).
*Style length.*—0.3 cm.

Disc florets:

*Color.*—RHS N92B (Violet-blue).
*Shape.*—Tubular.
*Apex.*—Rounded.
*Surface.*—Smooth, shiny.
*Size.*—Length: 0.5 cm. Width: 0.7 cm.
*Stamens.*—5, fused into a single tube.
*Anther color.*—RHS N92A (Violet-blue).
*Anther length.*—0.1 cm.
*Anther shape.*—Oval.
*Pollen color.*—RHS 155A (White).
*Pollen amount.*—Moderate.
*Filament color.*—RHS 17A (Yellow-orange).

Disease and insect resistance: Very disease resistant, however, plants are susceptible to aphids, thrips, whiteflies and worms.

Seed and fruit production: None observed.

COMPARISON WITH PARENTAL LINES AND KNOWN CULTIVARS

'SAKOST190' is a distinct variety of *Osteospermum* owing to its cream to shell-pink flower color, and vigorous, compact growth habit. 'SAKOST190' is distinguished from its parents primarily by cream to shell-pink flower color, and vigorous, compact growth habit as described in Table 1 (color references are to The Royal Horticultural Society Colour Chart, 4$^{th}$ edition):

TABLE 1

| Comparison with Parental Lines | | | |
|---|---|---|---|
| Characteristic | 'SAKOST190' | Male Parent 'SL-4' | Female Parent 'V-59' |
| Ray floret (ligule) color, upper surface: | Yellow-White (RHS 158C) with Violet-blue (RHS N92D) and Purple (RHS N78C) at base to bottom of base; streaks of RHS N78D (Purple) on the ray floret and the tip of the ray floret. | Lemon yellow | Pink-white bicolor |

TABLE 1-continued

| Comparison with Parental Lines | | | |
|---|---|---|---|
| Characteristic | 'SAKOST190' | Male Parent 'SL-4' | Female Parent 'V-59' |
| Performance under high temperature and humid conditions | Very vigorous | Maintains ability to bloom under high temperature conditions, but lacks tolerance to high humidity. | Maintains ability to bloom under high humid conditions, does not maintain flowering under high temperatures. |

'SAKOST190' is most similar to the *Osteospermum* plant 'Sevamil' (U.S. Plant Pat. No. 14,708); however, there are differences as described in Table 2 (color references are to The Royal Horticultural Society Colour Chart, 4$^{th}$ edition):

TABLE 2

| Comparison with Similar Variety | | |
|---|---|---|
| Characteristic | 'SAKOST190' | 'Sevamil' |
| Ray floret (ligule) color, upper surface: | Yellow-White (RHS 158C) with Violet-blue (RHS N92D) and Purple (RHS N78C) at base to bottom of base; streaks of RHS N78D (Purple) on the ray floret and the tip of the ray floret. | Yellow (RHS 11D) with Purple (RHS 79B to RHS 79C) towards base. |
| Ray floret (ligule) color, lower surface: | Greyed-Orange (RHS 164C) with streaks of Greyed-Purple (RHS N187B) and Violet-Blue (RHS 93C) at base. | Yellow (RHS 13B) with fine Greyed-Green longitudinal stripes (RHS 191C to RHS 191D) |
| Disc florets color | Violet-Blue (RHS 92B) | Purple (RHS 79A) |
| Performance under high temperature and humid conditions | Very vigorous | Vigorous |

I claim:

1. A new and distinct cultivar of *Osteospermum* plant as shown and described herein.

* * * * *